United States Patent [19]

Simeon et al.

[11] Patent Number: 5,139,482

[45] Date of Patent: Aug. 18, 1992

[54] FLUID INFUSION LINE MONITOR

[76] Inventors: Paula S. Simeon, 718 Highland Ave., Glendale, Calif. 91202; Donald E. Lewis, 543 Bradbury Rd., Monrovia, Calif. 91016

[21] Appl. No.: 735,699

[22] Filed: Jul. 25, 1991

Related U.S. Application Data

[63] Continuation-in-part of Ser. No. 467,024, Jan. 18, 1990, abandoned.

[51] Int. Cl.$^5$ ............................................. A61M 25/01
[52] U.S. Cl. ............................. 604/66; 128/DIG. 13
[58] Field of Search ................................. 604/65-67, 604/253; 128/DIG. 13; 356/436; 250/573; 417/4

[56] References Cited

U.S. PATENT DOCUMENTS

| | | | |
|---|---|---|---|
| 2,835,252 | 5/1958 | Mauchel | 604/65 |
| 3,163,176 | 12/1964 | Darling | 604/65 |
| 3,935,876 | 2/1976 | Massie et al. | 137/177 |
| 4,010,749 | 3/1977 | Shaw . | |
| 4,181,610 | 1/1980 | Shintani et al. . | |
| 4,213,454 | 7/1980 | Shim | 604/65 |
| 4,312,341 | 1/1982 | Zissimopoulos et al. | 604/67 |
| 4,397,648 | 11/1980 | Knute | 604/253 |
| 4,530,696 | 7/1985 | Bisera et al. . | |
| 4,565,500 | 1/1986 | Jeensalute et al. . | |
| 4,570,639 | 2/1986 | Miodownik | 128/718 |
| 4,743,228 | 5/1988 | Butterfield . | |
| 4,816,695 | 3/1989 | Lavin | 250/573 |
| 4,829,448 | 5/1989 | Balding et al. | 364/509 |
| 4,884,065 | 11/1989 | Crouse et al. | 340/632 |

FOREIGN PATENT DOCUMENTS 2830512 1/1980 Fed. Rep. of Germany .
2207998 2/1989 United Kingdom .

OTHER PUBLICATIONS

IBM Tech. Bulletin, E. R. Ellenwood, vol. 12, No. 5, Oct. 1969.

*Primary Examiner*—Randall L. Green
*Assistant Examiner*—Mary Beth O. Jones
*Attorney, Agent, or Firm*—Sheldon & Mak

[57] ABSTRACT

An apparatus for signalling an accidental loss of blood from a patient's fluid infusion line includes a sensor assembly for connection to the line, the assembly having a housing for receiving a portion of the line within a side opening, a holder having a clamp member for drawing together portions of the housing on opposite sides of the side opening for fixing the portion of the line within the opening relative to the housing, a source of radiation directed through the opening for intersecting the line, and a radiation detector in the housing for receiving radiation that is transmitted from the source through the line. The apparatus further includes a battery powered circuit, the circuit intermittently powering the radiation source, and producing a reference voltage, a train of signal pulses forming a sensor signal that is indicative of the radiation received by the detector and, when the sensor signal is in a predetermined relationship with the reference signal, an alarm signal. The alarm signal is produced by an audio output transducer, a switch for powering the transducer being responsive to the signal pulses and enabled by a train of output enable pulses that are synchronized with the activation of the radiation source for producing a distinctive audio output.

9 Claims, 1 Drawing Sheet

U.S. Patent
Aug. 18, 1992
5,139,482
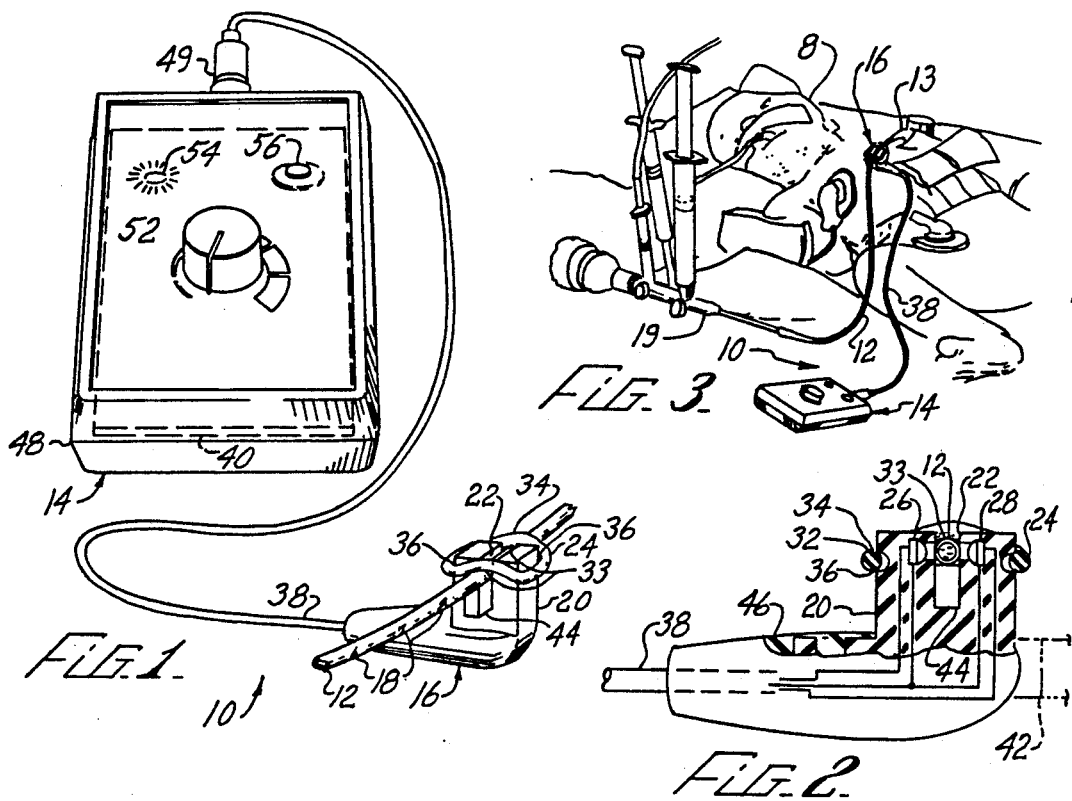
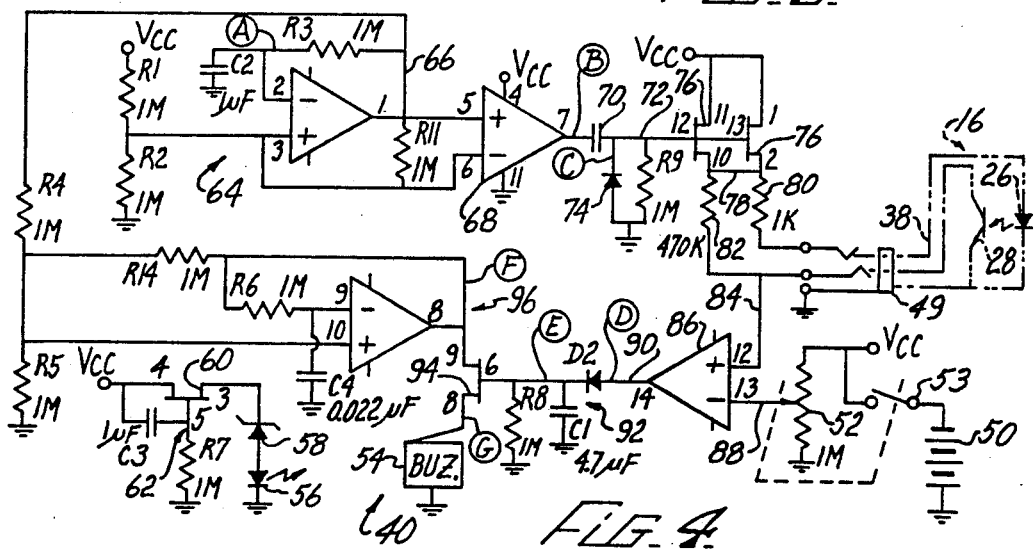

FLUID INFUSION LINE MONITOR

This application is a continuation-in-part of application Ser. No. 07/467,024, filed Jan. 18, 1990 now abandoned.

BACKGROUND

The present invention relates to the fail-safety of fluid-handling medical equipment, and more particularly to a fluid infusion line monitor.

It is very important to insure that equipment used to treat a patient is functioning properly and not placing a patient's safety in jeopardy. Iatrogenic (hospital induced) blood loss can produce severe deleterious physiological consequences for a patient as well as potential liability for health care providers. Both adults and infants can become quite ill from accidental bleeding though an inadvertently disconnected fluid line. An infant is noted to have worse effects from acute blood loss than an adult because an infant has less compensatory physiological protection than an adult and can lose a significant portion of his blood volume quickly. This danger is present, for example, when infants are provided with an umbilical artery catheter (UAC). These UACs are inserted by sterile procedure into an infant's umbilical stump vessels and have proven invaluable in the management of critically ill neonates. They are used to obtain blood for laboratory analysis, as a central conduit for fluid administration, for cardiac studies as well as for blood pressure determination. Occasionally, catheters may become accidentally disconnected due to patient activity, human error, or equipment malfunction, and via this unobserved disconnection, an infant may quickly lose a significant portion of his blood volume. Although a catheter is necessary for medical management of a sick infant, iatrogenic blood loss through the catheter would negate its therapeutic effects.

Adults are generally physiologically better equipped to compensate for an acute blood loss and may be able to communicate with hospital personnel in case of an accidental disconnection of a fluid infusion line causing blood loss. However, an adult may be extremely emotionally sensitive to his blood loss; consequently it is important to guard against accidental blood loss in any use of fluid infusion catheters.

Thus there is a need for a way to monitor the condition of a patient's fluid infusion line that is effective and reliable for preventing an accidental loss of blood from the patient, that is easy to use and inexpensive to provide.

SUMMARY

The present invention is directed to an apparatus for signalling an alasm condition in a patient's fluid catheter line that meets these needs. The apparatus includes a sensor assembly for connection to the catheter line, the assembly including a housing having a passage therein for receiving a portion of the line and a side opening for laterally inserting the line, a ring-shaped clamp member retaining the portion of the line within the passage, the clamp member contacting the line at spaced apart locations proximate opposite ends of the passage, a radiation source, means for directing the radiation from the source through the opening for intersecting the line, and a radiation detector in the housing for receiving radiation that is transmitted from the source through the line; and circuit means for connecting to the sensor assembly, including a source of electrical power, means for producing a reference voltage, means for producing a sensor signal that is indicative of the radiation received by the detector, and means for producing an alarm signal when the sensor signal is in a predetermined relationship with the reference signal. The line is advantageously visible within the passage through the clamp member 32 for monitoring a desired positioning of the line within the passage, the clamp member encircling the passage without covering the passage. Thus indicia that might be present on the line can be reliably positioned away from the optical path of the sensor. As used herein, the term "alarm condition" means any condition requiring corrective action, such as an improper substance in the line as when there is an accidental loss of blood from the patient, or an improper flow rate of fluid in the line.

The housing can be formed with a pair of outwardly facing slots for releasably holding portions of the clamp member in a predetermined location on the housing. Preferably the clamp member is elastically tensioned, enclosing portions of the housing and partially enclosing the line at the spaced camp contact locations for inexpensively and reliably securing the line. Further, the housing can have a supporting member rigidly protruding therefrom at opposite ends of the passage for supporting the line against pressure from the clamp member proximate the spaced clamp contact locations. Moreover, the supporting member is preferably formed of a translucent material that extends through the housing in facing relation with the line for facilitating proper placement of the line by admitting ambient light for backlighting indicia on the line that might interfere with proper operation of the sensor. Thus the line is more easily positioned with such indicia to one side of an optical path of the sensor.

The source of electrical power can include a battery, the circuit means also having means for intermittently powering the radiation source whereby the sensor signal forms a train of signal pulses, the means for producing the alarm signal being responsive to the signal pulses. The means for intermittently powering the radiation source can include means for generating a quasi-triangle wave, first comparator means for generating a train of sensor enable pulses, and electronic switch means for repetitively connecting the source to the radiation source in response to the sensor enable pulses. The means for producing the alarm signal can have an audio output transducer, switch means for powering the output transducer in response to the signal pulses, means for generating a train of output enable pulses that are synchronized with the sensor enable pulses for powering the switch means, thereby producing a distinctive audio output.

DRAWINGS

These and other features, aspects, and advantages of the present invention will become better understood with reference to the following description, appended claims, and accompanying drawings, where:

FIG. 1 is an oblique elevational perspective view of a fluid infusion line monitor according to the present invention;

FIG. 2 is a fragmentary sectional elevational view of the monitor within region 2 of FIG. 1;

FIG. 3 is a perspective view showing the monitor of FIG. 1 in use on an infant's umbilical artery catheter;

FIG. 4 is a schematic circuit diagram of the monitor of FIG. 1; and

FIG. 5 is a circuit timing diagram of the monitor of FIG. 1.

DESCRIPTION

The present invention is directed to a patient infusion line monitor for alerting medical personnel in case disconnection or other malfunction of an intravenous tubing, infusion or catheter line. With reference to FIGS. 1-4 of the drawings, a monitor apparatus 10 for a patient infusion line 12 includes an alarm unit 14 and a sensor unit 16, the sensor unit 16 being removably attached to the infusion line 12 and electrically connected to the alarm unit 14. The infusion line 12 can be any translucent tubular member; typically, such lines are made from a flexible transparent material, and have indicia 18 thereon for facilitating a determination of a rate of fluid flow through the line 12. Also, the infusion line 12 usually forms a portion of a catheter, such as an umbilical artery catheter (UAC) 13 for an infant 8 as shown in FIG. 3. UACs provide a convenient central path for fluid administration, for cardiac studies, and for blood pressure determination, the catheter 13 being connected to an infusion manifold 19. A catheter suitable for use as a UAC and having the infusion line 12 with the indicia 18 as described above is available in sizes 3 ½, 5, and 8 (size 5 being most commonly used for infants) from Argyle Division of Sherwood Medical, of St. Louis, Mo.

As best shown in FIG. 2, the sensor unit 16 includes a housing 20 having a side opening 22 for receiving the infusion line 12, and clamp means 24 for removably retaining the line 12 fixed relative to the housing 20. Within the housing 20 and on opposite sides of the opening 22 are an infrared emitter 26, and a photodetector 28 for receiving radiation from the emitter 26 that passes through the infusion line 12, an optical path being defined between the emitter 26 and the detector 28. According to the present invention, the sensor unit 16 is responsive to changes in light transmission characteristics of a fluid within the infusion line 12. In particular, a relatively greater light transmission occurs through a typical infusion fluid than through blood that can get into the infusion line 12 in the event that the line 12 malfunctions or becomes disconnected.

It is important to retain the infusion line 12 fixed within the housing 20 for preventing changes in the light transmission characteristics of the infusion line 12 between the emitter 26 and the photodetector 28 that might be introduced by movement of the indicia 18 with the line 12 within the opening 22. As shown in FIG. 2, the clamp means 24 is provided by a clamp member 32 that contacts the infusion line 12 proximate opposite ends of the opening 22, as indicated at 33 in FIGS. 1 and 2, whereby the infusion line 12 is gripped within the opening 22. The clamp member 32 is formed as an O-ring 34 from a suitable resilient material such as Neoprene ®, and the housing 20 is formed with a pair of slots or grooves 36 for releasably retaining the O-ring 34 on opposite sides of the opening 22. In case of a malfunction, the sensor unit 16 can be easily and quickly removed from the infusion line 12, for replacement.

A multi-conductor electrical cable 38 extends between the housing 20 and the alarm unit 14 for electrically connecting the emitter 26 and the photodetector 28 to a control circuit 40 within the alarm unit 14. The housing 20, including the emitter 26 and the photodetector 28 can be fabricated by appropriate modification of a commercially available sensor module, such as sensor Model TIL159 which has been available from Texas Instruments of Houston, Tex. Second source devices also suitable are available as Models HOA 1872-11 and HOA 1872-12 sensors from Honeywell Microswitch division, Honeywell Inc., Freeport, Ill. It is believed that at least one of the devices available from Sensor Integrated Systems of Plano, Tex., as SenIsys Models S-870N55, S-871N55, and S-872N55 is also suitable. As further shown in FIG. 2, the housing 20 is made by removal of one mounting flange 42 (if present) of the TIL159 sensor, and forming the grooves 36 therein. Also, a spacer member 44 is inserted within the side opening 22 for spacing the infusion line 12 in line between the emitter 26 and the photodetector 28. The spacer member 44 can be made from a suitable plastic material, such as Plexiglas ®, and bonded in place with an appropriate adhesive. As shown in FIG. 1, the spacer member 44 extends beyond opposite ends of the side opening 22 for enhanced support of the infusion line 12 under the contacting portions of the O-ring 34 relative to the housing 20. The material of the spacer member 44 being transparent or translucent as in the case of Plexiglas ® advantageously permits the line 12 to be backlighted from ambient light, the spacer member 44 extending beyond opposite ends of the housing 20 and facing the line 12 as described above. Thus the spacer 44 facilitates placement of the line 12 with the indicia 18 not blocking the optical path between the emitter 26 and the photodetector 28, thereby enhancing the visibility of the indicia 18 through the opening 22 and the clamp member 32.

As best shown in FIG. 1, the O-ring 34 is located by the grooves 36 at an elevation relative to the opening 22 that is below the top of the infusion line 12, the O-ring 34 flexing upwardly in tension and bending over the line 22, at the contact locations 33 as best shown in FIG. 1. With the cable 38 electrical-y connected to the emitter 26 and the photodetector 28 in a conventional manner, a cable support 46 is formed about the cable 38 proximate the housing 20, the support 46 being formed of a suitable resilient material and bonded to the housing 20.

The alarm unit 14 includes a case 48 for the control circuit 40, the cable 38 being removably connected to the control circuit 40 by means of a 3-conductor phone jack 49 that protrudes the case 48. As shown in FIG. 4, the control circuit 40 includes a battery 50 for providing a suitable source of electrical power and as also shown in FIG. 1, a potentiometer control 52 for adjusting an alarm trigger level of the apparatus 10, an audio alarm transducer or buzzer 54, and an indicator light 56 for verifying sufficient battery voltage. As further shown in FIG. 4, the potentiometer control 52 has an associated power switch 53 for selectively connecting the battery 50 to the other parts of the control circuit 40. Also, the battery 50 can be a conventional 9-volt transistor battery, the indicator light 56 being connected in series with a zener diode 58 for preventing operation of the light 56 when the battery 50 is discharged below a predetermined voltage. In the circuit of FIG. 4, the diode 58 has a zener voltage of 5 volts, and the indicator light 56 is colored green for providing a green indication when the battery voltage is at or above approximately 6.5 volts. An indicator driver 60 having an associated RC network 62 is also connected in series with the indicator light 56 for indicating proper battery voltage at the initial turn on time, the network 62 disabling the driver 60 after approximately 2 seconds for prolonging the life of the battery 50.

The control circuit 40 includes a first operational amplifier 64, the first operational amplifier 64 being connected for generating a square wave oscillator output 66, at a frequency on the order of 0.2 Hz, the amplifier 64 having an associated quasi-triangle input as shown in FIG. 5 by the signal labelled "A". A first comparator 68, responsive to the oscillator output 66, is connected through a series capacitor 70 for driving a pulse enable line 72, a grounded rectifying diode 74 also being connected to the enable line 72 for preventing negative excursions thereon. The output waveform of the first comparator is labeled "B" in FIGS. 4 and 5, and the waveform of the enable line 72 is similarly labeled "C". A pair of parallel-connected driver switches 76, responsive to the enable line 72, repetitively operate a pulse power line 78, the pulse power line 78 being separately connected to the emitter 26 and the photodetector 28 of the sensor unit 16, respectively, through an emitter resistor 80 and a detector resistor 82. Thus the sensor unit 16 is pulsed at a duty cycle of less than 5 percent, rather than powered continuously, for greatly reducing the overall current drain from the battery 50. Significantly, the greatest instantaneous current drain within the apparatus 10 is through the emitter 26, at least while no alarm condition is being signalled by the buzzer 54.

The photodetector 28 variably loads the detector resistor 82, producing a corresponding detector signal 84. A second comparator 86 is responsively connected to the detector signal 84 and an alarm trigger input 88 from the potentiometer control 52, the trigger input 88 having a reference voltage thereon that corresponds to the alarm trigger level as set by the potentiometer control 52.

Accordingly, when an alarm condition is present as a result of blood, for example, blocking light transmission from the emitter 26 to the photodetector 28, the detector signal 84 is repetitively pulsed to a potential in excess of the voltage of the trigger input 88, thereby producing a corresponding train of positive pulses on a detector output 90 of the second comparator, as indicated at "D" in FIG. 5. The detector output 90 is connected through a rectifying filter 92 for integrating the detector output 90 as indicated at "E" in FIG. 5, thereby driving a buzzer switch 94, for activating the buzzer 54 when the alarm condition is present.

The buzzer switch 94 is powered by a second operational amplifier 96, the second operational amplifier 96 being connected for producing a square wave "F" of appropriate duty cycle in response to the quasi-triangle wave output 66 of the first operational amplifier 64 such that a distinctive "cricket-like" chirping sound is produced by the buzzer 54 when the waveforms "E" and "F" are simultaneously activated as indicated at "G" in FIG. 5. A buzzer suitable for use as the buzzer 54 in the present invention is a MiniLert® continuous tone buzzer.

A preferred configuration of the control circuit 40 can be implemented using low power CMOS integrated circuits for the indicator driver 60, the driver switches 76, and the buzzer switch 94. In particular, each of the elements listed above can be combined as shown in FIG. 4 in a single CMOS quad switch such as a conventional CD4066 integrated circuit that is commercially available from a variety of sources. Similarly, the operational amplifiers 64 and 96 together with the comparators 68 and 86 can be combined in a single low power integrated circuit such as an LM324 quad operational amplifier, as also shown in FIG. 4. For even longer battery life, a TL064 low power version of the LM 324 can be used.

As shown in FIG. 3, the monitor apparatus 10 of the present invention is conveniently compatible with typical health care environments, being portable and electrically isolated from other patient care apparatus and associated equipment. For example, the apparatus 10 can be used in surgery, critical care ICUs, dialysis and home infusion therapy. The size of the infusion line 22 is not critical as long as the line 12 is accepted within the opening 22 without being blocked, in that the clamp member 32 biasingly holds the line 12 against the spacer member 44, the line 12 being partially enclosed at the spaced clamp contact locations 33 for security against twisting and/or lateral movement relative to the housing 20. Moreover, the apparatus 10 can be used in non-medical applications such as in industrial process and manufacturing where the patency of a fluid line is considered important.

Although the present invention has been described in considerable detail with reference to certain preferred versions thereof, other versions are possible. For example, the sensor unit 16 could be made as an integral part of a catheter, the emitter 26 and photodetector 28 being located at a terminal end outside of the patient. Also, the grooves 36 can be interrupted, being formed locally at corners of the housing 20. Further, the control circuit 40 can be adapted for signalling or regulating the rate of fluid flow in the infusion line 12. Moreover, the housing 20 can be formed with the opening 22 enlarged for accepting larger tubing of the infusion line 12, such as that commonly used with adult patients. Therefore, the spirit and scope of the appended claims should not necessarily be limited to the description of the preferred versions contained herein.

What is claimed is:

1. An apparatus for signalling an alarm condition in a patient's fluid catheter line, comprising:
   (a) a sensor assembly for connection to the catheter line, comprising:
      (i) a housing having a passage therein for receiving a portion of the line, the passage having a side opening laterally inserting the line;
      (ii) means for retaining the portion of the line in a fixed position with the passage, comprising a ring-shaped clamp member for selectively clamping the line relative to the housing at spaced apart clamp contact locations on the line proximate opposite ends of the passage, the line being visible through the clamp member for monitoring a desired positioning of the line within the passage;
      (iii) a radiation source;
      (iv) means for directing the radiation from the source through the opening for intersecting the line; and
      (v) a radiation detector in the housing for receiving radiation that is transmitted from the source through the line; and
   (b) circuit means for connecting to the sensor assembly, comprising:
      (i) a source of electrical power;
      (ii) means for producing a reference voltage;

(iii) means for producing a sensor signal, the sensor signal being indicative of the radiation received by the detector; and (iv) means for producing an alarm signal when the sensor signal is in a predetermined relationship with the reference signal.

2. The apparatus of claim 1 wherein the housing is formed with a pair of outwardly facing slots for releasably holding a portion of the clamp member in a predetermined location on the housing.

3. The apparatus of claim 2 wherein the clamp member encloses portions of the housing on opposite sides of the passage, the clamp member being elastically tensioned and partially enclosing the catheter line at the spaced clamp contact locations.

4. The apparatus of claim 1, wherein the source of electrical power comprises a battery, the circuit means further comprising means for intermittently powering the radiation source whereby the sensor signal forms a train of signal pulses and the means for producing the alarm signal is responsive to the signal pulses.

5. The apparatus of claim 4, wherein the means for intermittently powering the radiation source comprises means for generating a quasi-triangle wave, first comparator means for generating a train of sensor enable pulses, and electronic switch means for repetitively connecting the source to the radiation source in response to the sensor enable pulses.

6. The apparatus of claim 5, wherein the means for producing the alarm signal comprises an audio output transducer, switch means for powering the output transducer in response to the signal pulses, means for generating a train of output enable pulses, the output enable pulses being synchronized with the sensor enable pulses, the output enable pulses powering the switch means for producing a distinctive audio output.

7. The apparatus of claim 1, further comprising a supporting member rigidly protruding form the housing at opposite ends of the passage for supporting the line against the clamp member proximate the spaced clamp contact locations.

8. The apparatus of claim 7, wherein the supporting member is formed of a translucent material, the member extending through the housing in facing relation with the line for facilitating proper placement of the line by backlighting same.

9. An apparatus for signalling an accidental loss of blood from a patient's fluid infusion line, comprising:

(a) a sensor assembly for connection to the infusion line, comprising:
  (i) a housing having a passage therein for receiving a portion of the line, the passage having a side opening for laterally inserting the line, the housing being formed with a pair of outwardly facing slots on opposite sides of the passage;
  (ii) means for holding the portion of the line within the opening in fixed relation to the housing, comprising a ring-shaped clamp member for selectively clamping the line relative to the housing at spaced apart clamp contact locations on the line proximate opposite ends of the passage, the line being visible through the clamp member for monitoring a desired positioning of the line within the passage, the clamp member engaging the slots and enclosing portions of the housing, the clamp member being elastically tensioned and partially enclosing the line at the spaced clamp contact locations;
  (iii) a radiation source;
  (iv) means for directing the radiation from the source through the opening for intersecting the line; and
  (v) a radiation detector in the housing for receiving radiation that is transmitted from the source through the line; and (b) circuit means for connecting to the sensor assembly, comprising:
  (i) means for connecting a battery for providing a source of electrical power;
  (ii) means for producing a reference voltage;
  (iii) means for producing a sensor signal, the sensor signal being indicative of the radiation received by the detector;
  (iv) means for intermittently powering the radiation source whereby the sensor signal forms a train of signal pulses; and
  (v) means for producing an alarm signal when the sensor signal is in a predetermined relationship with the reference signal, the means for producing an alarm signal comprising an audio output transducer, switch means for powering the output transducer in response to the signal pulses, means for generating a train of output enable pulses, the output enable pulses being synchronized with the sensor enable pulses, the output enable pulses powering the switch means for producing a distinctive audio output.

* * * * *